United States Patent [19]
Niven et al.

[11] Patent Number: 6,022,737
[45] Date of Patent: Feb. 8, 2000

[54] FORMULATIONS FOR NON-VIRAL IN VIVO TRANSFECTION IN THE LUNGS

[75] Inventors: Ralph Niven, Camarillo; Daniel J. Freeman, Thousand Oaks, both of Calif.

[73] Assignee: Amgen Inc., Thousand Oaks, Calif.

[21] Appl. No.: 08/556,780

[22] Filed: Nov. 2, 1995

[51] Int. Cl.$^7$ .......................... C12N 15/63; C12N 15/00; C12N 5/00; A01N 43/04
[52] U.S. Cl. .................. 435/320.1; 435/455; 435/325; 435/69.1; 424/93.21; 514/44
[58] Field of Search .............................. 424/450, 93.21; 514/44, 2; 435/172.3, 320.1, 455, 325, 69.1; 530/350

[56] References Cited

U.S. PATENT DOCUMENTS 5,811,406  9/1998  Szoka, Jr. et al. ...................... 514/44

FOREIGN PATENT DOCUMENTS

95/00128  1/1995  WIPO .

OTHER PUBLICATIONS

Bout, et al., "Lung Gene Therapy: *In Vivo* Adenovirus–Mediated Gene Transfer to Rhesus Monkey Airway Epithelium", *Human Gene Theraphy*,5: 3–10 (1994).
Canonico, et al., "No Lung Toxicity After Repeated Aerosol or Intravenous Delivery of Plasmid–Cationic Liposome Complexes", *J. Appl. Physiol.,*77: 415–419 (1994).
Felgner, et al., "Synthetic Recombinant DNA Delivery for Cancer Therapeutics", *Cancer Gene Therapy,* 2(1): 61–65 (1995).
Han, et al., "Suppression of In Vivo Tumorigenicity of Human Lung Cancer Cell by Retrovirus–Mediated Transfer of the Human Tumor Necrosis Factor–$\alpha_c$DNA", *Am. J. Respir. Cell Mol. Biol.,*11: 270–278 (1994).
Hazinski, Thomas A., "Prospects for Gene Therapy in Acute Lung Injury",*Am. J. Med. Sciences,*304(2): 131–135 (1992).
Morita, et al., "Effect of Various Absorption Promoters on Pulmonary Absorption of Drugs with Different Molecular Weights", *Biol. Pharm. Bull.,* 16(3): 259–262 (1993).
Stewart, et al., "Gene Transfer *In Vivo* With Dna–Liposome Complexes: Safety and Acute Toxicity in Mice", *Human Gene Therapy,* 3: 267–275 (1992).
Stribling, et al., "Aerosol Gene Delivery In Vivo," *Proc. Natl. Acad. Sci. USA,*89: 11277–11281 (1992).
Orkin et al. Report and Recommendations of the Panel to Assess the NIH Investment in Research on Gene Therapy, Dec. 7, 1995.

Treco et al., Molecular Medicine Today, pp. 314–321, 1995.
Eck & Wilson, 'Gene–Based Therapy' in Goodman & Gilman's The Pharmacological Basis of Therapeutics. Ninth Edition, McGraw–Hill: New York, pp. 77–101, 1995.
Shao et al., Eur. J. Pharm. Biopharm., 40(5):283–288 (1994).
Cabral–Marques et al., J. Pharm. Pharmacol., 42:13P (1990).
de Robertis et al., Bioorganic & Medicinal Chemistry Letters, 4(9):1127–1130 (1994).
Cabral–Marques et al., International Journal of Pharmaceutics, 77:297–302 (1991).
Myers et al., Experimental Lung Research, 19:1–19 (1993).
Meyer et al., Gene Therapy, 2:450–460 (1995).
Hazinski et al., Am. J. Respir. Cell Mol. Biol., 4:206–209 (1991).
Yoshimura et al., Nucleic Acids Research, 20(12):3233–3240 (1992).
McLachlan et al., Gene Therapy, 2:614–622 (1995).
Bout et al., Experimental Lung Research, 19:193–202 (1993).
Tsan et al., American Journal of Physiology, 268(6):L1052–L1056 (1995).
Li et al., Drug Development and Industrial Pharmacy, 20(12):2017–2024 (1994).
Freeman et al., Pharmaceutical Research, 13(2):202–209 (1996).
Niven et al., Journal of Controlled Release, 32:177–189 (1994).
Niven et al., Pharmaceutical Research, 11(8):1101–1109 (1994).
Freeman et al., Pharmaceutical Research, 12(Suppl.9):S312 (1995).
Yamamoto et al., J. Pharm. Pharmacol., 46:14–18 (1994).
Fukuda et al., Biol. Pharm. Bull., 18(6):891–894 (1995).
Morita et al., Drug Delivery System, 6(3):207–211 (1991).
Kawahara et al., Proc. Intern. Symp. Control. Rel. Bioact. Mater., 22:604–605 (1995).
Niven et al., Drugs Pharm. Sci., 54:321–359 (1992).
Niven et al., Critical Reviews in Therapeutic Drug Carrier Systems, 12(2&3)151–231 (1995).

*Primary Examiner*—Deborah Crouch
*Assistant Examiner*—Jill D. Martin
*Attorney, Agent, or Firm*—Craig A. Crandall; Ron K. Levy; Steven M. Odre

[57] ABSTRACT

Formulations useful in improving non-viral in vivo transfection of DNA in the lungs are provided. Formulations which comprise DNA with various additives are prepared and delivered to the lungs resulting in production of a transcription product.

8 Claims, 7 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: unknown
      (D) TOPOLOGY: unknown (ii) MOLECULE TYPE: DNA (xi) SEQUENCE DESCRIPTION: SEQ ID NO:1:

GGAACCTTAC TTCTGTGGTG TG                              22

(2) INFORMATION FOR SEQ ID NO:2:

(i) SEQUENCE CHARACTERISTICS:
      (A) LENGTH: 21 base pairs
      (B) TYPE: nucleic acid
      (C) STRANDEDNESS: unknown
      (D) TOPOLOGY: unknown (ii) MOLECULE TYPE: DNA (xi) SEQUENCE DESCRIPTION: SEQ ID NO:2:

CTTGGGGTCT TCTACCTTCT C                                21

FORMULATIONS FOR NON-VIRAL IN VIVO TRANSFECTION IN THE LUNGS

TECHNICAL FIELD

The present invention relates to methods and formulations useful in improving non-viral in vivo transfection of DNA in the lungs, which comprise DNA with various additives.

BACKGROUND OF THE INVENTION

Advances in molecular cloning techniques have led to the identification and isolation of an expanding array of genes with mutations responsible for human diseases. Such advancements have made it possible to consider gene transfer, i.e., replacement of absent or mutated genes, as a potential treatment for certain genetic and/or acquired disorders.

Traditional gene therapy approaches utilize ex vivo gene transfer; Liebert et al., *Human Gene Therapy*, 2:251–256 (1991). Ex vivo approaches involve transformation of cells in vitro with DNA (the cells having first been harvested from the patient and grown in culture), followed by introduction of the transformed cells back into the patient. In such techniques, in vitro transfer is generally done using retrovirus-based vectors; Zwiebel et al., *Science*, 243:220–222 (1989). Ex vivo gene therapy looks quite promising; however, such therapy is obviously limited by the fact that it can only be used to transfect a limited number of cells and cannot be used to transfect cells which are not first removed from the body.

A theoretically more attractive gene therapy approach currently under investigation is direct gene transfer technology, i.e, direct introduction of a gene transfer vector into a target organ in vivo. This technique utilizes purified gene sequences as drug molecules in a manner similar to the way conventional pharmaceutical agents are administered. Currently, both viral-based and nonviral-based DNA transfer methods are being tested in vivo, with a variety of purified genes, and in a variety of clinical settings.

At present, direct gene transfer technology is being extensively studied in the treatment of pulmonary disorders. The lung is a particularly attractive organ for such therapy because it is directly accessible via the airways, is isolated from other organ systems, and its anatomy allows for different routes of administration to be contemplated. In vivo transfection of lung tissue after administration of genes to the lungs has been achieved by a variety of means; see e.g., Canonico et al., *J. Appl. Physiol.*, 77:415–19 (1994); Stewart et al., *Hum. Gene Ther.*, 3:267–75 (1992); Wilson et al., *Hum. Gene Ther.*, 5:1019–57 (1994). Vector systems have included adenoviruses; see e.g., Brody et al., *Ann N.Y. Acad. Sci.*, 716:90–101 (1994); Mastrangeli et al., *J. Clin. Invest.*, 91:225–34 (1993), retroviruses; Han et al., *Am. J. Respir. Cell Mol. Biol.*, 11:270–78 (1994), and liposome based complexes; Stewart et al., *Hum. Gene Ther.*, 3:267–75 (1992) and references cited therein.

These demonstrations of transfection and production of protein illustrate the promise that in vivo gene therapy of the lung may have; however, there are still many crucial problems that need to be addressed before such therapy can prove to be a realizable goal. For example, viral approaches, while appearing to be the most efficient in terms of DNA transfer, are likely to be severely limited due to immunogenicity, especially where repeat dosing is expected. Furthermore, the fact that retroviruses can only transfect dividing cells and must integrate into the host cell chromosome for transcription to occur, brings into question the safety of in vivo use of such vectors, in particular, the possibility of recombination with endogenous viruses, which could in turn mutate into a deleterious infectious form. Finally, there are likely to be substantial formulation, scale up and manufacturing problems associated with use of virus-based vectors.

Non-viral techniques, although less likely to cause a host reaction, have so far demonstrated poor transfection efficiency in vivo. For example, techniques utilizing DNA-liposome complexes to transfer genes require large doses of DNA and lipid in order to detect even minute levels of protein after instillation in the lungs; Stribling et al., *P.N.A.S. USA*, 89:11277–81 (1992). Likewise, aerosol delivery to animals and humans is a highly inefficient process in that 80% to 90% of the starting material can be wasted irrespective of the inhalation device employed. These transfection efficiency problems must be overcome in order to make in vivo gene transfer using nonviral vectors clinically applicable. Resolution of the transfection efficiency problem requires that large quantities of inexpensive DNA plasmid be readily available and/or a formulation be found that dramatically improves protein production in vivo.

SUMMARY OF THE INVENTION

Accordingly, it is one object of the present invention to provide formulations and methods for improving non-viral in vivo transfection of DNA in the lungs. The formulations of the present invention include a transfection agent, said agent prepared by forming a mixture comprising a DNA plasmid and an additive, wherein said DNA plasmid includes a DNA sequence capable of producing a transcription product in a mammalian cell transfected by said transfection agent, and wherein said additive is selected from the group consisting of permeation enhancers, peptides, lipids, growth factors, surfactants, mucolytic polymers, and positively charged polymers. The formulations of the present invention will significantly advance the development of gene-based therapies for the treatment or therapy of the human body.

DETAILED DESCRIPTION OF THE INVENTION

Figure 1:
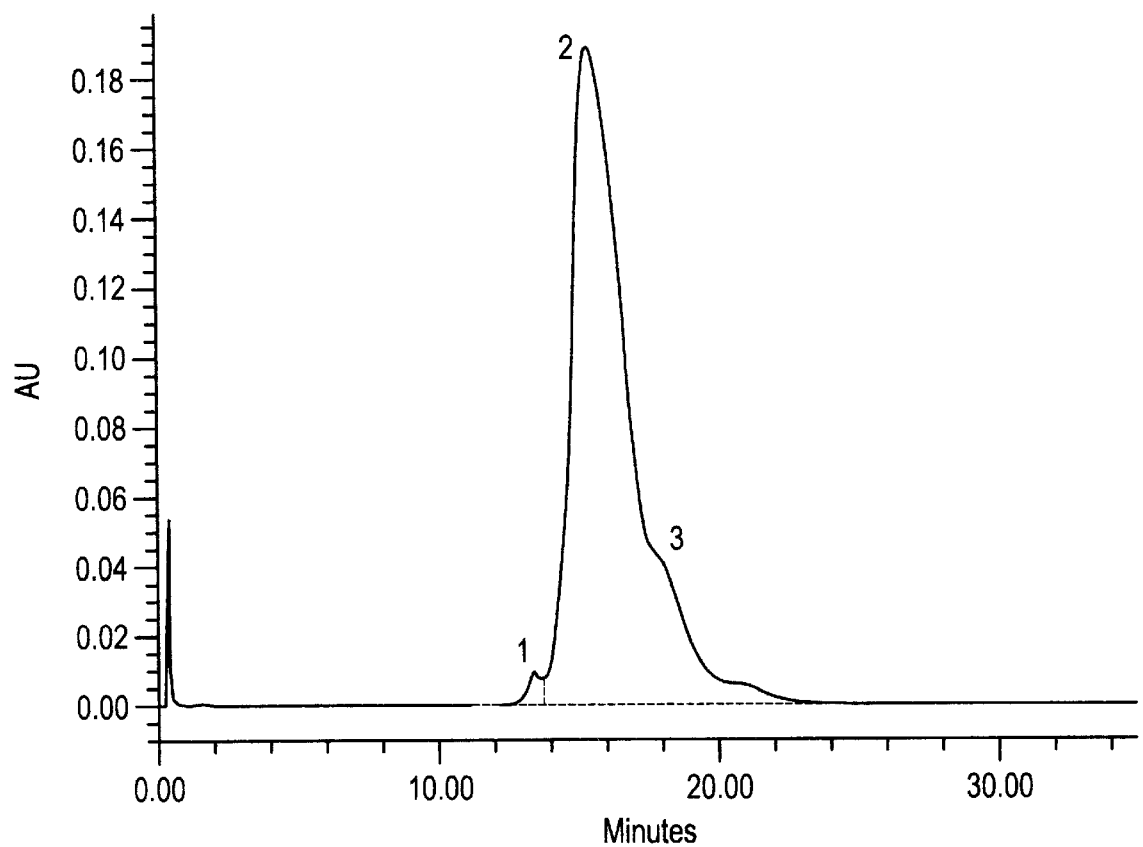
FIG. 1 represents the chromatogram from the anion exchange column used to purify a plasmid used in the present working examples. Resolution time (in minutes) is plotted versus Absorbance Units (AU). Peak 1 represents the open-circular form of DNA, Peak 2 the main supercoiled DNA, and Peak 3 is thought to represent genomic DNA.

In accordance with the present invention, formulations and methods are provided which allow for improved non-viral in vivo transfection of DNA in the lungs. The present invention grew out of studies in which a plasmid containing the luciferase "marker" cDNA was constructed and used to test non-viral gene delivery formulations in vivo. Formulations comprising luciferase DNA plus various additives, in a solution, or in the form of a spray-dried powder, were administered via intratracheal instillation (IT) or were administered in the form of a powder via intratracheal insufflation (IF). These formulations were tested for their ability to promote luciferase production in the lungs. Several formulations were found to improve in vivo transfection as compared to DNA alone, and one particular formulation, containing DNA plus the additive sodium glycocholate, was found to provide dramatically improved in vivo transfection of DNA in the lung.

The term "transfection agent" as used herein, means any agent which is capable of transfecting mammalian cells, using a non-viral vector system, and then expressing a therapeutic agent for treating an adverse condition of the human body. Preferably, the transfection agent includes a DNA plasmid and an additive, wherein said DNA plasmid comprises a DNA sequence capable of producing a transcription product in a mammalian cell transfected by said agent. More preferably, said DNA plasmid contains a sequence which expresses a therapeutic agent for treating an adverse condition of the lung.

Suitable additives which may be employed include, but are not limited to, peptides, lipids, growth factors, permeation enhancers, surfactants, mucolytic polymers, and positively charged polymers.

In one aspect of the invention, the additive is a permeation enhancer. Permeation enhancers which may be employed include bile salts such as sodium glycocholate and other molecules such as β-cyclodextrin. Bile salts are known to increase the absorption of macromolecules across membranes; Pontiroli et al., *Diabet. Metab.,* 13:441–43 (1987) and also act as protease inhibitors; Morita et al., *Pharm. Res.,* 11:909–13 (1994). Molecules such as β-cyclodextrin have been used primarily as "solublizing" agents for drugs of low aqueous solubility; Brewster et al., *Pharm. Res.,* 8:792–795 (1991) and have also been found to enhance uptake of albuterol from the lungs; Marques et al., *Int. J. Pharm.,* 77:303–307 (1991). In a particularly preferred embodiment, the transfection agent comprises plasmid DNA and the additive, sodium glycocholate.

DNA plasmids useful in the present invention include those which include DNA sequences which code for antioxidants such as glutathione peroxidase and superoxide dismutase; protease inhibitors such as human alpha-1-antitrypsin, TIMP-1, TIMP-2, TIMP-3 and SLPI; and various tumor suppressor genes. Also contemplated are DNA plasmids which include DNA sequences which code for potent cytokines, including various hematopoietic factors such as G-CSF, GM-CSF, M-CSF, MGDF, the interferons (alpha, beta, and gamma), interferon consensus, the interleukins (1–12), erythropoietin (EPO), fibroblast growth factor, TNF, TNFbp, IL-1ra, stem cell factor, nerve growth factor, GDNF, BDNF, NT3, platelet-derived growth factor, and tumor growth factor (alpha, beta) and leptin.

The formulations of the present invention are contemplated for use in gene therapies for the treatment or therapy of the human body. Particularly contemplated are various lung disorders. For example, formulations comprising plasmid DNA encoding certain antioxidants or protease inhibitors may be useful in preventing acute lung disorders, e.g., pulmonary emphysema and adult respiratory distress syndrome, or any other instance where lung cells are undergoing oxidant stress. Further, there is increasing evidence from syngenic murine cancer models that the induction of local production of a variety of cytokines by tumor cells can result in suppression of tumor cell growth; see e.g., Asher et al., *J. Immunol.,* 146:3227–3234 (1991); Karp et al., *J. Immunol.,* 149:2076–2081 (1992), and therefore, formulations comprising DNA plasmids encoding various cytokines could be useful in a lung cancer therapy.

The formulations of the present invention may be in solution or in the form of a spray-dried powder. The spray-dried powders are prepared using procedures well known by those skilled in the art; see e.g., Broadhead et al., *Drug Dev. and Indust. Pharmacy* 18:1169–1206 (1992) and references cited therein. In one aspect of the present invention, the DNA powder was formulated by spray-drying in conjunction with trehalose. It was envisioned that this change in state might provide a means to concentrate DNA molecules within localized regions of the airway and alveolar epithelium during dissolution of deposited particles, and thus increase the cellular uptake of DNA simply on the basis of a large number of DNA molecules being present in the vicinity of the cell surface.

The routes of administration contemplated for use with the formulations of the present invention include parenteral injection, intratracheal delivery, and aerosol delivery. The particular route of administration utilized will be readily determined by one skilled in art, based on factors such as the condition being treated, and the specific lung tissue being targeted.

The formulations of the present invention may also include pharmaceutically acceptable diluents, preservatives, solubilizers, emulsifiers, adjuvants and/or carriers. Such compositions will influence the physical state, stability, and bioavailability of the protein. See, e.g., *Remingtons Pharmaceutical Sciences,* 18th Edition, (Mack Publishing Co., Easton, Pa., 1990) which is herein incorporated by reference. What constitutes an effective amount of the DNA in a particular case will depend on a variety of factors which the knowledgeable practitioner will take into account, including the desired therapeutic result, the severity of the condition or illness being treated, the physical condition of the subject, and so forth.

The embodiments of the present invention are further exemplified by the examples provided below. Example 1 below describes the construction of a plasmid containing luciferase cDNA. Example 2 describes a scale up procedure which allowed for production of gram quantities plasmid DNA. Example 3 describes the purification and characterization of the DNA, and the preparation of various DNA/additive formulations. Example 4 describes the protocol used for the in vitro testing of DNA+DC Chol:DOPE formulations. Example 5 describes the protocol used, and results obtained for the in vivo gene transfer experiments. Example 6 describes the results obtained for in vivo gene transfer experiments using spray-dried formulations. Example 7 describes in vivo transfection dose-response experiments performed with DNA+sodium glycocholate formulations. Example 8 describes experiments designed to evaluate the toxicities associated with intratracheal instillation of DNA+sodium glycocholate formulations. Example 9 provides mRNA analysis which helps to confirm transfection and determine how long expression levels are maintained.

As shown by in vivo gene transfer studies, the present formulations significantly increase protein production in the lungs following intratracheal administration.

EXAMPLE 1

This example describes the construction of the plasmid containing luciferase DNA. pGL2CMV, a luciferase expression plasmid vector driven by the human cytomegalovirus promoter, was constructed from pGL2 Basic, a firefly luciferase expression vector (Promega, Madison, Wis.) and CMVFF3, a human cytomegalovirus containing vector (Fox Chase Cancer Center, Philadelphia, Pa.). The plasmid pGL2 basic was linearized with XhoI restriction endonuclease at base number 33 in the polylinker, and made blunt ended with Klenow (New England Biolabs, Beverly, Mass.). Similarly, the hCMV promoter was removed from the CMVFF3 plasmid with HindIII and BamHI restriction endonucleases, and made blunt ended with Klenow. pGL2CMV was then prepared by ligating the hCMV fragment into the linearized pGL2 Basic plasmid. The orientation of the hCMV promoter in the plasmid was confirmed by a restriction digest of the SmaI site in the polylinker of the pGL2 Basic plasmid and the NcoI site at the 5' end of the hCMV fragment. Fragments were run on 1% agarose gels. All restriction endonucleases were purchased from Boehringer Mannheim, Indianapolis, Ind.

EXAMPLE 2

This example describes the scale up methodology used to prepare large quantities of the plasmid DNA used in the present invention.

Cell paste was grown in 10 liter fermentors to an optical density >100. Bacterial hosts were grown in Terrific broth supplemented with 100 μg/ml ampicillin. Eight hundred grams of the resulting cell paste was added to 25 liter of resuspension buffer (100 μg/ml RNase, 50 mM Tris base, and 10 mM EDTA at pH 8.0). Cells were mixed for 45 minutes at 4° C. and then added to 25 liters of lysing buffer (200 mM NaOH and 1% w/v SDS) and stirred for a further twenty minutes. Lysate was then precipitated with 25 liters of 3 M potassium acetate, pH 5.5 held at 4° C. The mixture was stirred for 60 minutes. 750 mg of filter aid 521 was added to the precipitated lysate to aid filtering through a prewetted CUNO 10SP filter (Cuno, France) at a flow rate of 2 liter/minute. Back pressure was monitored and held at <35 psig. The DNA was precipitated from the filtered lysate with 0.8 volumes of isopropanol (4° C.) and was then 'dead-end-screen', filtered onto a Sartopure GF 1.2 μm filter (Sartorius, Edgewood, N.Y.) at a flow rate of 500 ml/min. After loading, DNA was back-flushed off the filter with 10 liter of loading buffer (10 mM Tris-HCl, 1mM EDTA, 50 mM NaCl, pH 8.5) at a flow rate of 250 ml/min. The time required to back-flush was determined by monitoring the UV absorbance at 260 and 280 nm. Once absorbance dropped to background, flow was halted and the DNA was removed for purification.

EXAMPLE 3

This example describes the purification and characterization of the DNA, and the preparation of various DNA/additive formulations.

1. DNA Purification and Characterization

DNA separation was carried out on a Biopilot FPLC (Pharmacia Biotech Inc., Piscataway, N.J.) in a BPG 200/500 column (Pharmacia Biotech) using Q-Sepharose high performance anion exchange gel (Pharmacia Biotech). The DNA was loaded onto the column at 13 cm/hr. Excess debris was subsequently washed through the column with 10 column volumes of loading buffer. The loading buffer was then exchanged with a "low salt", buffer (10 mM Tris-HCl, 1 mM EDTA, 0.6 M NaCl, pH 8.0) using a five column volume linear gradient. DNA was eluted over a twenty column volume gradient with "high salt" buffer (10 mM Tris-HCl, 1 mM EDTA, 0.9 M NaCl, pH 8.0) at 13 cm/hr. The DNA eluted at approximately 0.73 M NaCl. The chromatogram for this anion exchange column is depicted in FIG. 1.

A commercial endotoxin (LPS) removal kit (Qiagen) was used to remove bacterial endotoxins from the DNA. The resultant 'clean' material was then screened for LPS using the limulus amebocyte lysate (LAL) test; Bacterial Endotoxins Test [85], *USP Pharmacopeia*, 23:1696–97 (1995). Representative samples from each lot of DNA were run on 1% agarose gels (Seakem LE; FMC, Rockland, Me.) @ 100 v, 50 mA for one hour(Bio-rad mini sub cell and Bio-rad Power Pac 300, Bio-rad Labs, Hercules, Calif.) to insure the DNA retained its double stranded, supercoiled form. A typical agarose gel is provided in FIG. 2.

Figure 2:
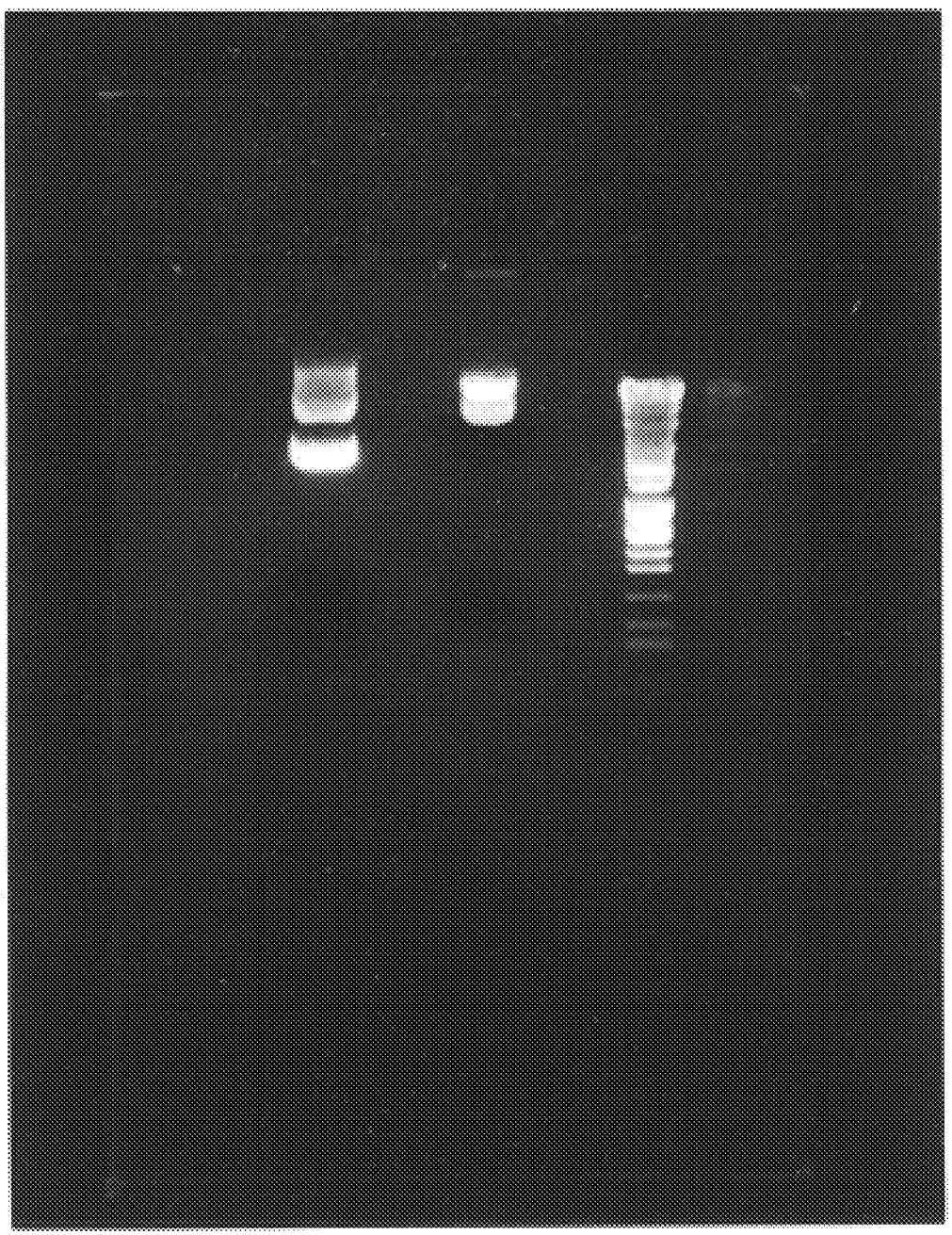
FIG. 2 is a photograph of a representative agarose gel in which supercoiled DNA plasmid used in the present working examples (lane 1, band C), open-circular DNA plus genomic DNA (lane 2, bands B and A), and molecular weight markers (lane 3) are depicted.

As demonstrated by FIGS. 1 and 2, the plasmid was resolved as several peaks and bands, with one dominating (peak 2, and lane 1, band C, respectively). A 'denatured' form of the DNA, induced by enzyme nicking is shown in lane 2, band B of FIG. 2 illustrating open-circular DNA and perhaps the presence of some genomic DNA (lane 2, band A). Open-circular DNA was also resolved as a fronting-peak in the chromatogram (peak 1). Genomic DNA may also be represented on the chromatogram as the shoulder on the back side of the main peak (peak 3). The fact that the 'purified' DNA causes transfection in vitro and in vivo as seen below suggests that the majority of the plasmid is 'biologically active'.

2. Preparation of DNA Formulations

A. DNA-Lipid

DNA-lipid mixtures were prepared with lipid concentrations of dioleoyl phosphatidylethanolamine (DOPE)(Avanti Polar Lipids, Alabaster, Ala.) to [N-(N',N'-dimethylaminoethane)carbamoyl]cholesterol (DC Chol)(1:1 mole ratio). The DC Chol was synthesized and the liposomes formed as described by Gao and Huang, *Biochem. and Biophys. Res. Commun.*, 179:280–85 (1991). The DC Chol was characterized by thin layer chromatography (TLC) and infra red spectroscopy (IR)(Perkin Elmer 1600 series, Norwalk, Conn.). For TLC, a mobile phase of 65:35 $CHCl_3$:MeOH by volume was used and samples were identified with iodine vapor and ninhydrin. A single spot was resolved indicating that the lipid was intact. For IR, a nugol mull was prepared and scanned from 450–4500 cm$^{-1}$.

To form liposomes, the DOPE and the DC Chol were combined in chloroform and dried over nitrogen gas. Further drying was performed for 3 hours in an evacuated desiccator. The lipid film was subsequently hydrated with distilled water over a period of 2 hours. During this hydration period, the dispersion was sonicated at intervals of 5 minute (15 minute total) using an ultrasonic water bath. The dispersion was allowed to cool on ice between each sonication period. DNA, at the appropriate amount, was mixed in solution with the formed liposome dispersion within 30 minutes of dosing cells or animals.

B. DNA Powder

Spray-dried powders were prepared using a modified Buchi 190 spray-drier as described by Niven et al., *Pharm. Res.*, 11:1101–1109 (1993). Solutions containing 0.2% w/v plasmid and 1.8% trehalose in water were atomized at a rate of 1.5 ml/min into the drier using an atomization air pressure of 70 psig (10 literair/min) and a drying air-volume of approximately 600 liter/min. Inlet and outlet air temperatures were 135° C. and 91° C., respectively. The dew point of the drying air was approximately −75° C. The resulting powder was assessed for size and morphology using centrifugal photosedimentation (Horiba CAPA 300, Horiba Inc., Irvine, Calif.), and scanning electron microscopy (JSM 5200, Jeol Inc., Peabody, Mass.). The stability of the plasmid after reconstitution of the powder in water was checked using agarose gels as described above. Rats were dosed via insufflation with a nominal powder dose of 2 mg.

3. DNA+Additives

200 μg DNA was combined with a number of additives within 30 minutes prior to dosing the animals. The various additives and dosage regimens used in the in vivo studies are set forth in Table 1 below. Keratinocyte growth factor (KGF) and epidermal growth factor (EGF)(Sigma) were administered 24 hour before dosing the plasmid alone.

TABLE 1

| Compound | Dose[a] | | Mass ratio |
| --- | --- | --- | --- |
| | mg/ml | mg/kg | |
| DNA alone | 1.0 | 0.8 | — |
| Trehalose powder[b] | — | 7.2 | 1:9 |
| NaGC | 100 | 80.0 | 1:100 |
| | 10.0 | 8.0 | 1:10 |
| | 5.0 | 4.0 | 1:5 |
| | 1.0 | 0.8 | 1:1 |
| | 0.1 | 0.08 | 10:1 |
| KGF | 10 | 10.0 | — |
| EGF | 5 | 5.0 | — |
| Tween 80 | 10.0 | 8.0 | 1:10 |
| DC Chol:DOPE[c] | 8.0 | 6.4 | 1:8 |
| N-acetyl cysteine | 100 | 80.0 | 1:100 |
| β-cyclodextrin | 10.0 | 8.0 | 1:10 |
| PVAVAM 15%[d] | 35.2 | 8.8 | 1:44 |
| PVAVAM 6% | 35.2 | 8.8 | 1:44 |

[a]A total volume of 200 μl was dosed to each animal. With the exception of the "DNA alone" row, the data refers to the additive only
[b]Amount of sugar (1.8 mg) combined in the spray dried particles containing the DNA
[c]Liposomes formed in a 1:1 mole ratio
[d]Poly (vinylalcohol-co-vinylamine) was dosed in a total volume of 250 μl. The PVAVAM molecular weight was <5000 for these studies.

EXAMPLE 4

This example describes the protocol used and results obtained for the in vitro testing of DC Chol:DOPE+DNA formulations. This experiment was conducted to insure that in vitro transfection and luciferase production was capable with the DNA preparation to be used in the in vivo studies.

Cos-7, an SV40 virus transformed monkey kidney cell line, was obtained from the American Type Culture Collection (ATCC, CRL 1651) and maintained in DMEM (Gibco BRL, Gaitherburg, Md.) supplemented with 10% w/v BSA and 100 units/ml penicillin and 100 μg/ml streptomycin (Gibco BRI). For transfection studies, the Cos-7 cells were allowed to grow to ~80% confluency in a 6-well plate (Falcon Ware, Benton Dickinson, Franklin Lakes, N.J.). Cells were then transfected with DNA/DC Chol:DOPE formulations (liposomes formed in a 1:1 mole ratio). A total of 1 μg of plasmid pGL2CMV, or control plasmid pCMV-β-Gal, was added to cells after mixing the DNA with lipid. 1 ml was added to each well and after 24 hours, the media was removed and 300 μl of lysis buffer was added to each well. Cells were then assayed using commercial luciferase assay kit (Enhanced luciferase assay kit 1880 K, Analytical Luminescence Labs, San Diego, Calif.). Luciferase was detected using a luminometer (Monolight 2010, Analytical Luminescence Labs) where samples were read for 10 seconds. The results of the in vitro studies are depicted in FIG. 3.

Figure 3:
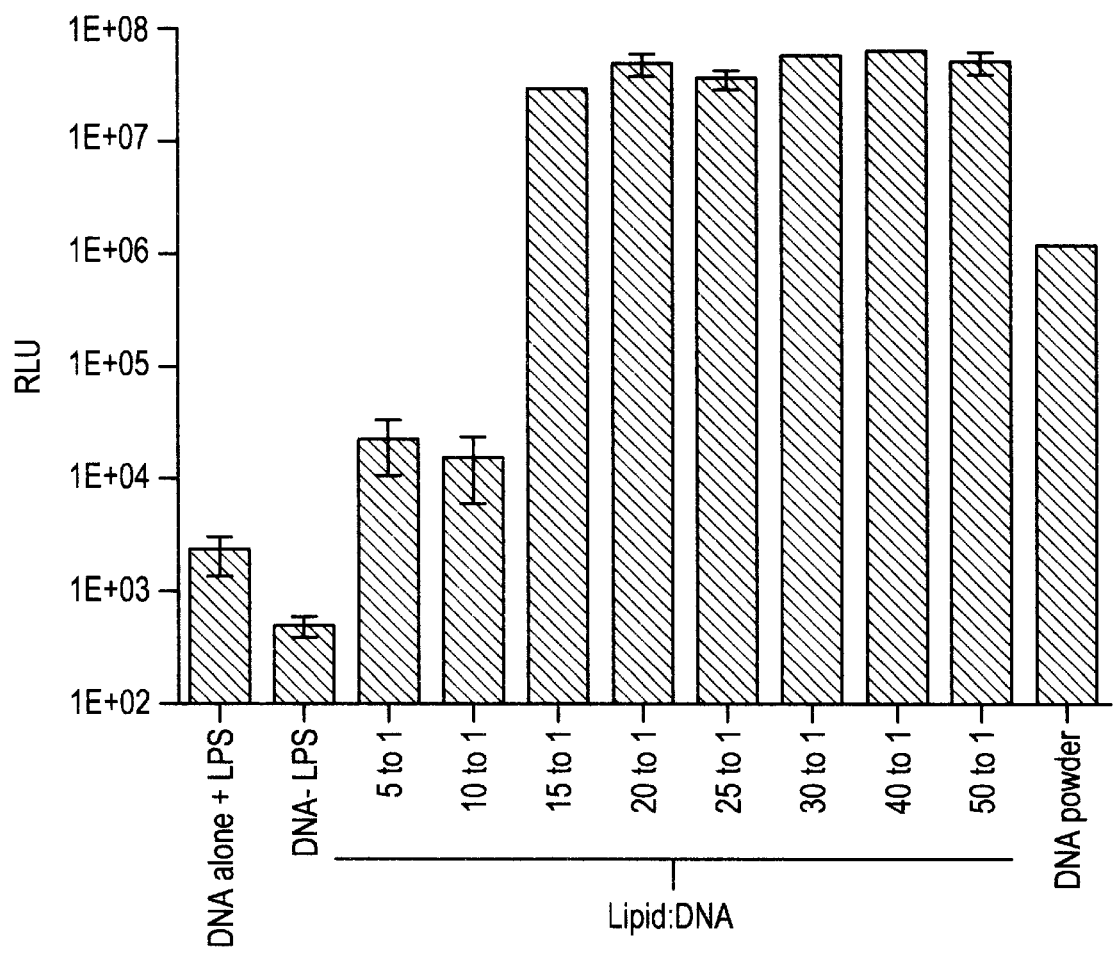
FIG. 3 is a bar graph representation of the in vitro transfection levels for the various DC Chol:DOPE (1:1)+ DNA formulations described herein (see Example 4), in Cos-7 cells. In vitro transfection is measured by the amount of luciferase detected by luminometry (RLU).

The FIG. 3 data indicate that the optimal lipid:DNA mass ratio for the DC Chol:DOPE lies between mass ratios of 20:1 to 50:1 with no significant transfection apparent at ratios less than 15:1. Higher ratios cause a reduction in transfection due to toxicity. The data also indicates that reconstituted spray-dried powder is capable of transfection after mixing with the lipid at a ratio of 40:1, however there is some reduction in transfection, suggesting that some activity is loss during spray-drying or during reconstitution of the plasmid. DNA alone did not cause luciferase production, and DNA that was not treated for LPS removal did not cause a substantial increase in transfection compared to treated plasmid.

EXAMPLE 5

This example describes the protocol used and results obtained, for the in vivo gene transfer experiments.

Adult male rats (Spague-Dawley) weighing approximately 250 grams were used for all in vivo experiments. Animals were quarantined for one week before being released for experimental use. Chow and water was provided ad libitum. The animals were dosed via intratracheal instillation (IT) or intratracheal insufflation (IF). The rats were initially incubated with the teflon sheaf of a Quik-Cath 18G 2" catheter (Baxter Health Care Corp., McGaw Park, Ill.). To instill, an 20 G 4" pipetting needle, connected to a 1 ml syringe containing approximately 200 μl of dosing solution, was inserted into the catheter. Dosing was completed by depressing the syringe plunger rapidly. To insufflate, a 'tube' containing 1 to 2 mg of powder was lodged inside the barrel of the catheter. A 5 ml syringe was then attached to the Luer end of the catheter and a 4 ml air bolus was used to force the powder into the lungs. The majority of experiments were performed using the instillation technique. Rats were sacrificed 24 hour post-dose.

Following euthanasia, the chest wall of the rats was opened and the lungs were resected en bloc. The pulmonary circulation was perfused via the pulmonary artery with 15–20 ml buffer (136 mM NaCl, 5.3 mM KCl, 5.6 mM glucose, 10 mM Hepes buffer, and 3 mM NaPO$_4$) gravity fed with 40 cm water pressure until clear of blood. The lungs were then dissected into 2 components. The 'left' side included the left and mediastinal lobes and the 'right' side included the right upper, middle and lower lobes. The lung lobes were homogenized (PT-MR 3000 Homogenizer, Polytron Kinematica, Littau, Switzerland) in 2 ml lysis buffer (0.1 ml potassium phosphate, pH 7.8, 1% w/w Triton X100, 1 mM DTT and 2 mM EDTA) for 30 seconds at 25,000 rpm. The homogenate was centrifuged at 15,000 rpm (Tomy MTX-150 centrifuge, Tomy Tech, Palo Alto, Calif.) at 4° C. for 5 minutes. A 50 µl aliquot was taken from each sample supernatant and assayed for luciferase as described previously. An estimate of luciferase recovery from lung homogenate was determined by spiking known amounts of protein into the trachea of dissected lungs and then following the same homogenization procedure. Assay values were compared with spiked values.

Figure 4:
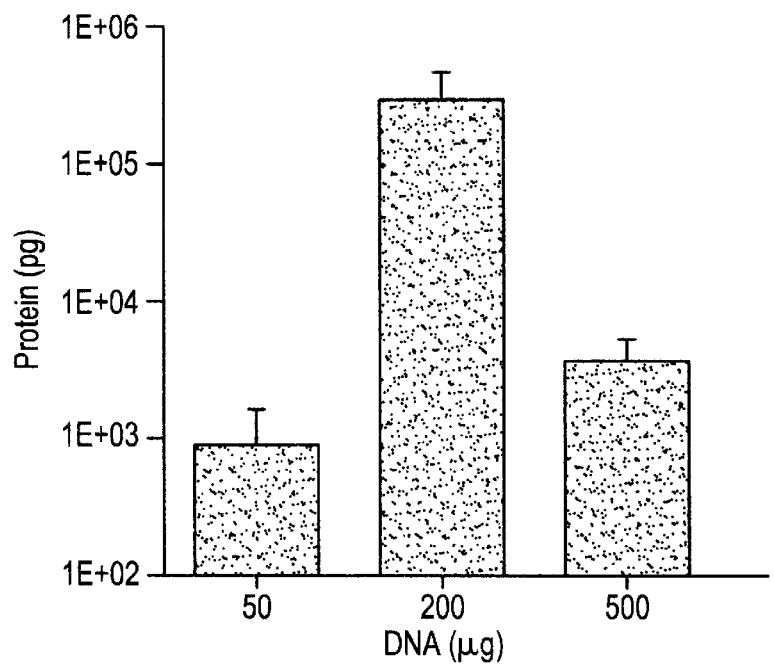
FIG. 4 is a bar graph representation of the dose-response data for the DNA plasmid alone obtained 24 hours after dosing (see Example 5). In vivo transfection is measured by the amount of luciferase detected by luminometry (RLU). The data shown represent the mean ± standard error of the mean.

Time course (24, 48 and 72 hours) and dose response (50, 200, and 500 µg DNA) studies were first conducted using the DNA plasmid alone. The results obtained 24 hours after dosing are set forth in FIG. 4. The data indicates that a dose of 200 µg DNA is capable of producing detectable levels of luciferase. The time course study indicated that 24 hours is optimal for detection of the flourochrome.

Figure 5:
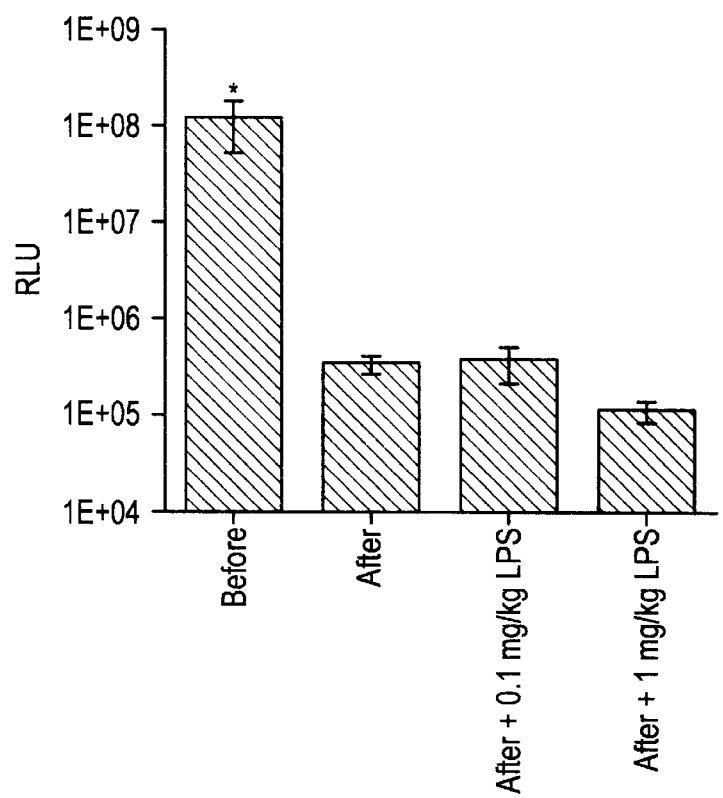
FIG. 5 is a bar graph representation of the results obtained for the experiments designed to study the effects of DNA 'purity' on in vivo transfection (see Example 5). In vivo transfection is measured by the amount of luciferase detected by luminometry (RLU).

Experiments were then conducted to compare in vivo transfection of DNA before and after treatment to remove LPS. In contrast to the in vitro data, DNA that is not treated to remove LPS causes a significant increase in luciferase production compared to treated DNA (see FIG. 5). However, the addition of LPS (0.1 mg/kg and 1 mg/kg) to treated DNA just before dosing did not restore transfection levels to those observed with untreated DNA (see FIG. 5). This suggests that while LPS may be a contaminant which leads to increased transfection, it is certainly not the only contaminant in the untreated DNA which influences transfection levels in the lung.

Figure 6:
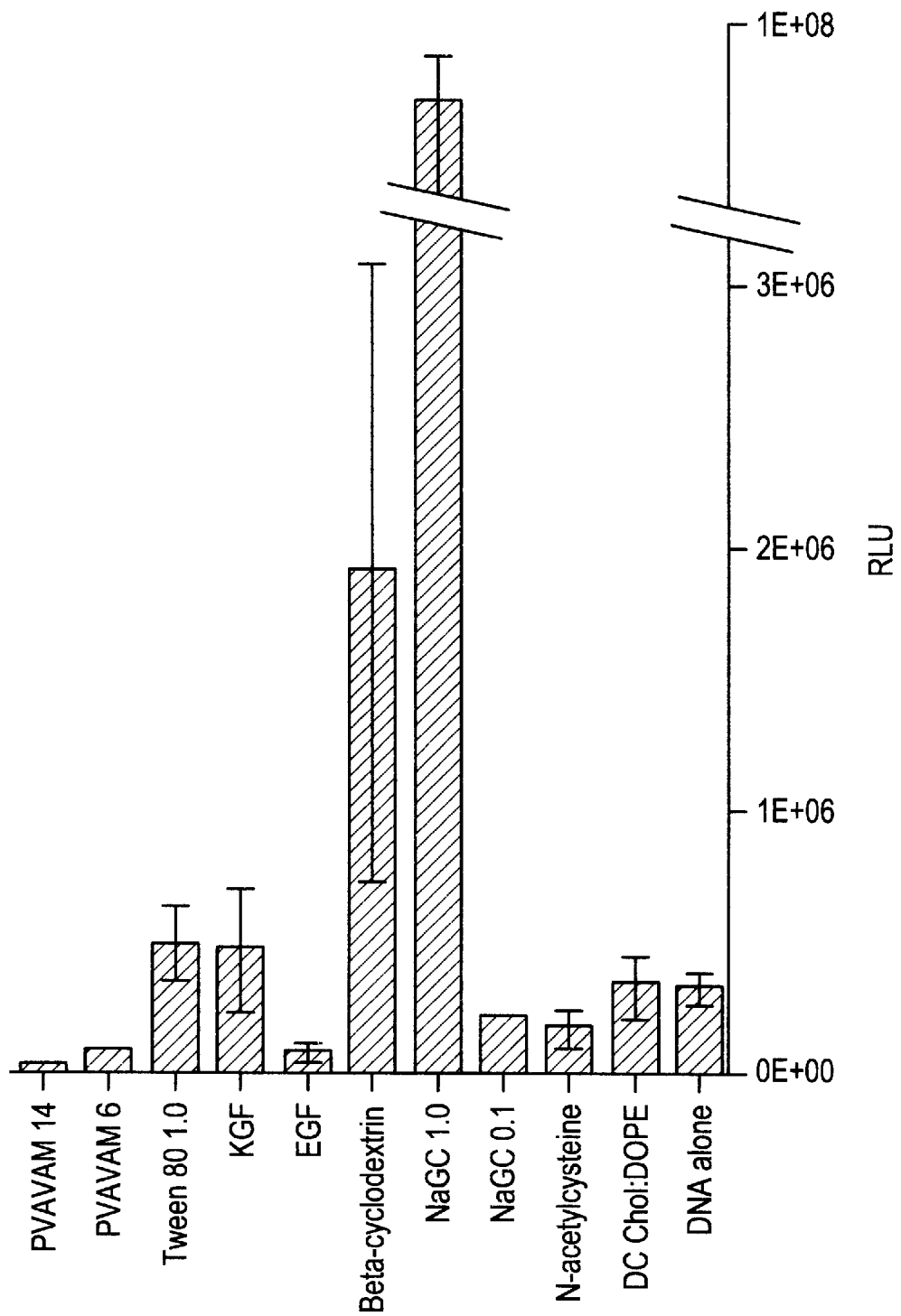
FIG. 6 is a bar graph representation of the in vivo transfection results obtained for the various DNA+ additive formulations (see Example 6). In vivo transfection is measured by the amount of luciferase detected by luminometry (RLU).

The DNA+additive formulations set forth in Table 1 above were then tested in the in vivo transfection studies. Based on the dose-response data, a nominal dose of 200 µg DNA was administered to the rats in these studies. For the EGF and KGF studies, rats were pretreated with each growth factor 24 hours before dosing the plasmid. The EGF dose of 5 mg/kg is a dose known to stimulate growth in lung epithelial cells; Schuger et al., *Dev. Biol.*, 159:462–73 (1993), and the KGF dose of 10 mg/kg is a dose known to induce hyperplasia of aveolar type II cells in rats; Ulich et al., *J. Clin. Invest.*, 93:1298–1306 (1994). The results of the in vivo transfection experiments are depicted in FIG. 6. The data indicate that the overall transfection capabilities of the different additives was generally variable and low; however, the enhancing effect of sodium glycocholate at a dose of 1% w/v was significant (~110 times higher vs. controls).

EXAMPLE 6

Figure 7:
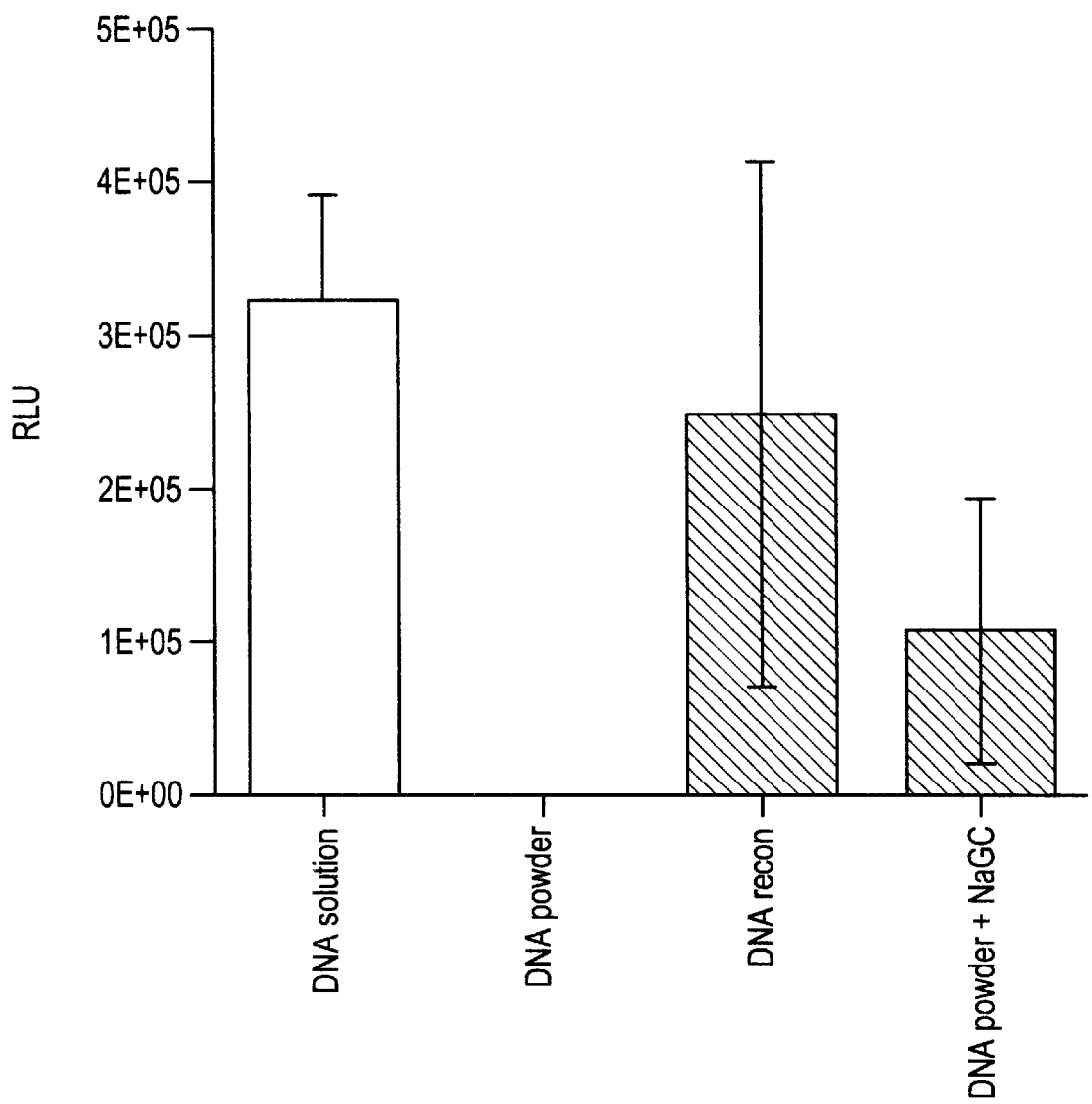
FIG. 7 is a bar graph representation of the in vivo transfection results obtained for spray-dried powders comprising DNA:trehalose (see Example 6). An instilled non spray-dried DNA solution, an insufflated DNA:trehalose powder, an instilled reconstituted DNA powder, and an insufflated DNA powder followed by instilled 1% w/v sodium glycocholate are depicted. In vivo transfection is measured by the amount of luciferase detected by luminometry (RLU).

This example describes the results obtained in in vivo gene transfer experiments using spray-dried formulations. DNA powder formulated by spray-drying in conjunction with trehalose was tested using IT and IF administration as described above. As depicted in FIG. 7, the reconstituted powder, when instilled into animals at a dose of ~200 µg plasmid alone, results in significant luciferase production, albeit at levels lower than the DNA solution. Unfortunately, no response is obtained with the insufflated DNA powder. This is probably due to the difficulty in administering sufficient powder as a bolus to the regions of the lung where transfection is occurring. However, when DNA powder is insufflated and then immediately followed by an instilled dose of 200 µl of 1% w/v sodium glycocholate, luciferase levels are increased, indicating that DNA powder can cause transfection in the lungs.

EXAMPLE 7

Based on the data obtained in the initial in vivo studies described in Example 5 above, a dose-response study using sodium glycocholate was conducted, and the results are set forth in Table 2.

TABLE 2

| Concentration | RLU | |
|---|---|---|
| % w/v | average | sem |
| 0 | $3.27 \times 10^5$ | $5.80 \times 10^3$ |
| 0.01 | $8.15 \times 10^4$ | $2.87 \times 10^3$ |
| 0.1 | $2.16 \times 10^5$ | $2.64 \times 10^3$ |
| 0.5 | $7.10 \times 10^6$ | $2.44 \times 10^6$ |
| 1.0 | $3.65 \times 10^7$ | $2.07 \times 10^6$ |

The results indicate that the enhancing effects of sodium glycocholate are, in fact, dose-dependent. The reason for the dramatic increase in transfection between the concentration range of 0.1% and 1.0% w/v may relate to formation of micelles. The critical micelle concentration (CMC) of sodium glycocholate in aqueous solution is around 9 mM or 0.45% w/v; Antonian et al., *J. Lipid Res.*, 31:947–51 (1990).

EXAMPLE 8

This example describes experiments designed to evaluate the toxicities associated with intratracheal instillation of sodium glycocholate+DNA formulations.

To evaluate the effects of the intratracheal instilled DNA in conjunction with 1% w/v sodium glycocholate, lung lavage and lung histology were performed 24 hour after dosing. After cannulating the trachea with an 18 G needle, lung lavage was performed with Dulbecco's phosphate buffered saline (Gibco BRL) through a 5 cc syringe (5×3 mL washes) and cytospin slides were prepared as described in Niven et al., *Pharm. Res.*, In press, 1995. Samples for histological analysis were also prepared by first cannulating the trachea as above, then perfusing the lungs with ~5 mL of zinc-formalin buffer (Baxter Health Care) using a pressure head of ~20 cm water. The lungs were fixed in 50 mL zinc formalin for six hours. After embedding and sectioning, slides were mounted and stained with hematoxylin and eosin.

These studies indicate that use of sodium glycocholate at higher concentrations result in significant mortality, possibly due to the increase in viscosity of the concentrated sodium glycocholate and perhaps some animals were asphyxiated, as most deaths occurred shortly after administration. In those animals examined for acute toxicity, the response was variable, with some animals characterized by compartmentalized but mild to heavy inflammation. Control animals receiving purified DNA alone did not show any abnormal histological features and, therefore, sodium glycocholate was responsible for the toxicity problems. Such toxicity concerns must certainly be taken into account when developing a gene therapy based on the use of bile salts as an additive.

EXAMPLE 9

This example describes experiments designed to confirm luciferase expression, and then determine how long expression levels were maintained.

mRNA was isolated after dosing with 200 µg DNA and 1% w/v sodium glycocholate and sacrificing animals at 12, 24 and 48 hours. Lungs were immediately removed and frozen in liquid nitrogen. After a brief thaw (~2 minutes), the tissue was homogenized as described above. Total RNA was then isolated from lung samples (RNeasy total RNA Purification Kit, Qiagen) and the luciferase RNA amplified by reverse transcription polymerase chain reaction (RTpcr) using a GeneAmp EZ rTth RNA PCR Kit (Perkins Elmer, Norwalk, Conn.). oligonucleotide primers used for RTpcr were 5'-GGAACCTTACTTCTGTGGTGTG-3' (SEQ ID NO.: 1 ) and 5'-CTTGGGGTCTTCTACCTTCTC- 3' (SEQ ID NO.: 2 ) and were obtained from Amgen Boulder, Inc.

Figure 8:
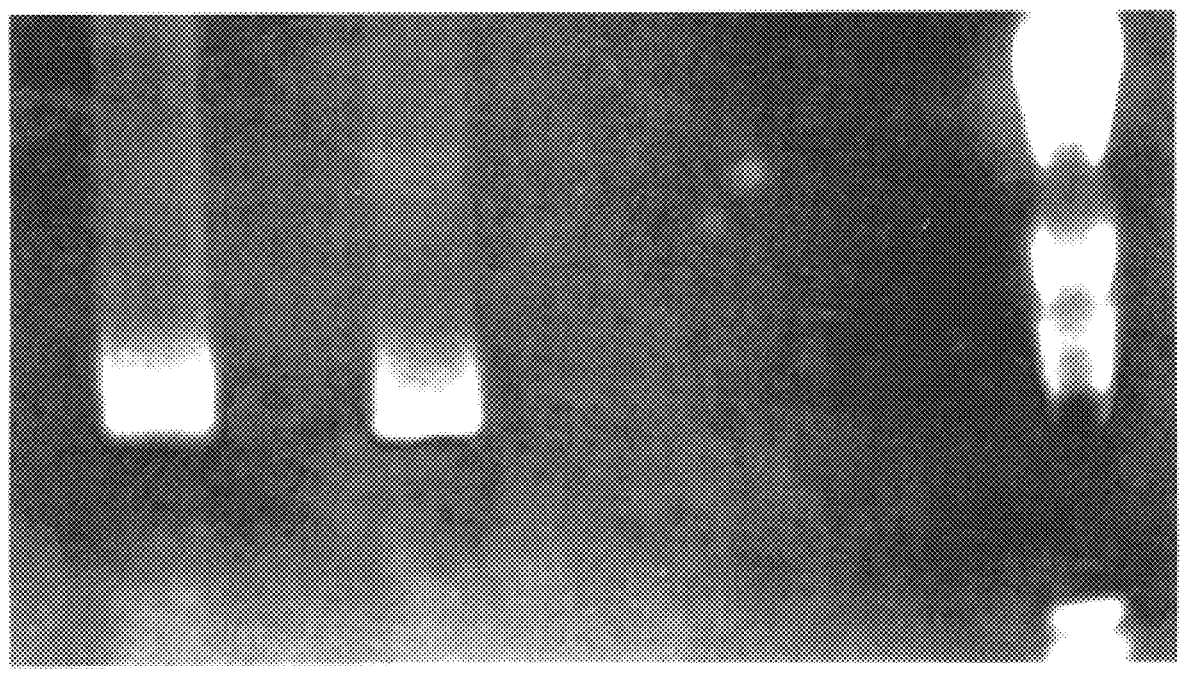
FIG. 8 is a photograph of an agarose gel in which luciferase mRNA detectable at 12 hours (lane 1), luciferase DNA detected at 48 hours (lane 2), untreated control (lane 3), and molecular weight markers (lane 4) are depicted (see Example 9).

As depicted in FIG. 8, the presence of luciferase mRNA is detectable in lung tissue 12 hr after dosing animals. The RTpcr mRNA should differ from the DNA by approximately 60 bp. Two bands are differentiated in the gel in FIG. 8 of approximately the bp size difference and this provides good evidence that indeed the luciferase mRNA has been detected. The mRNA was detectable 48 hr. after dosing indicating that the presence of luciferase at this time after dosing is not simply due to a prolonged half-life of the protein in lung tissue.

The data above demonstrate that DNA plus various additives can be used to deliver recombinant genes to the lung in vivo. The particular use of bile salts opens a new area of investigation and the use of sodium glycocholate at concentrations of 0.5 –1% w/v, could be useful in the treatment of various pulmonary disorders or with injectable preparations into tumors.

2. A transfection agent formulation according to claim 1, wherein said bile salt is sodium glycocholate.

3. A transfection agent formulation according to claim 1, wherein said DNA plasmid comprises a DNA sequence which encodes an antioxidant.

4. A transfection agent formulation according to claim 1, wherein said DNA plasmid comprises a DNA sequence which encodes a protease inhibitor.

5. A transfection agent formulation according to claim 1, wherein said DNA plasmid comprises a DNA sequence which encodes a tumor suppressor gene.

6. A transfection agent formulation according to claim 1, wherein said DNA plasmid comprises a DNA sequence which encodes a cytokine.

7. A transfection agent formulation according to claim 6, wherein said cytokine is selected from the group consisting of G-CSF, GM-CSF, M-CSF, MGDF, the interferons (alpha, beta, and gamma), interferon consensus, the interleukins (1–12), erythropoietin (EPO), fibroblast growth factor, TNF, TNFbp, IL-1ra, stem cell factor, nerve growth factor, GDNF, BDNF, NT3, platelet-derived growth factor, tumor growth factor (alpha, beta) and leptin.

8. A transfection agent formulation consisting of a DNA plasmid and β-cyclodextrin, wherein said DNA plasmid

What is claimed is:

1. A transfection agent formulation consisting of a DNA plasmid and a bile salt, wherein said DNA plasmid comprises a DNA sequence which encodes a transcription product, and wherein upon transfection of a mammalian cell, said DNA sequence is expressed such that said transfection agent effects intracellular delivery of said transcription product of at least two orders of magnitude higher than existing lipid-based formulations.

comprises a DNA sequence which encodes a transcription product, and wherein upon transfection of a mammalian cell, said DNA sequence is expressed such that said transfection agent effects intracellular delivery of said transcription product of at least two orders of magnitude higher than existing lipid-based formulations.

* * * * *